(12) United States Patent
Bálint (10) Patent No.: US 11,458,322 B2
(45) Date of Patent: Oct. 4, 2022

(54) DATA INTEGRITY FOR MEDICAL DEVICES USING BLOCKCHAIN SOLUTIONS

(71) Applicant: CereGate GmbH, Hamburg (DE)

(72) Inventor: Várkuti Bálint, Munich (DE)

(73) Assignee: CereGate GmbH, Hamburg (DE)

( * ) Notice: Subject to any disclaimer, the term of this patent is extended or adjusted under 35 U.S.C. 154(b) by 239 days.

(21) Appl. No.: 17/008,284

(22) Filed: Aug. 31, 2020

(65) Prior Publication Data

US 2021/0064605 A1 Mar. 4, 2021

(30) Foreign Application Priority Data

Sep. 1, 2019 (EP) ..................................... 19194812

(51) Int. Cl.
*H04L 29/06* (2006.01)
*A61N 1/372* (2006.01)
(Continued)

(52) U.S. Cl.
CPC ..... *A61N 1/37254* (2017.08); *G06F 16/2379* (2019.01); *G06F 21/577* (2013.01);
(Continued)

(58) Field of Classification Search
None
See application file for complete search history.

(56) References Cited

U.S. PATENT DOCUMENTS

| 2002/0065454 A1 * | 5/2002 | Lebel | A61N 1/37247 |
| | | | 607/2 |
| 2015/0117645 A1 | 4/2015 | Carlson et al. | |

(Continued)

FOREIGN PATENT DOCUMENTS

WO WO-2017198891 A1 * 11/2017 ........... A61B 5/6813

OTHER PUBLICATIONS

European Search Report, EPO Application No. 19194812.4-1122, dated Mar. 2, 2020, 10 pages.

*Primary Examiner* — Andrew J Steinle
(74) *Attorney, Agent, or Firm* — Rahman LLC (57) ABSTRACT

Methods and apparatus are provided for enhancing data integrity for implantable medical devices. A medical device is provided that is at least partially implantable. The medical device includes an application component configured to apply a therapeutic treatment and/or stimulation signals to a patient. The medical device includes a wireless communication transceiver and a computer memory storing a parameters library and computer readable instructions. A processor is configured to execute the computer readable instructions so as to perform the following steps: control application of therapeutic treatment and/or stimulation signals, via the application component, based on parameters stored in the parameters library; receive, via the wireless communications transceiver, update data representing an update to the parameters library from an external device or system; transmit at least the update data for verification by a blockchain network and addition of the update data to a verified blockchain public ledger including the update data; receive, via the wireless transceiver, blockchain public ledger data based on the verified blockchain public ledger; validate the update to the parameters library based at least on a first condition that the received blockchain public ledger data includes the update data; when the update to the parameters library is validated, control application of therapeutic treatment and/or stimulation signals, via the application component, based on parameters stored in the parameters library including the update data; and when the update to the parameters library is not validated, control the therapy application component so that the update data is not used.

15 Claims, 4 Drawing Sheets

(51) Int. Cl.
*G16H 40/67* (2018.01)
*G06F 16/23* (2019.01)
*H04B 1/3827* (2015.01)
*H04L 9/06* (2006.01)
*H04L 9/30* (2006.01)
*H04L 67/00* (2022.01)
*H04L 9/08* (2006.01)
*H04L 9/32* (2006.01)
*H04L 9/00* (2022.01)
*G06F 21/57* (2013.01)
*G16H 40/40* (2018.01)
*A61N 5/06* (2006.01)

(52) U.S. Cl.
CPC ............. *G16H 40/40* (2018.01); *G16H 40/67* (2018.01); *H04B 1/3827* (2013.01); *H04L 9/0637* (2013.01); *H04L 9/0822* (2013.01); *H04L 9/30* (2013.01); *H04L 9/3239* (2013.01); *H04L 9/50* (2022.05); *H04L 67/34* (2013.01); *A61N 2005/0626* (2013.01); *H04L 9/3247* (2013.01); *H04L 2209/88* (2013.01)

(56) References Cited

U.S. PATENT DOCUMENTS

| | | | |
|---|---|---|---|
| 2015/0332283 A1* | 11/2015 | Witchey | G06Q 10/10 705/3 |
| 2018/0176229 A1 | 6/2018 | Bathen et al. | |
| 2019/0200888 A1* | 7/2019 | Poltorak | A61B 5/0006 |

* cited by examiner

DATA INTEGRITY FOR MEDICAL DEVICES USING BLOCKCHAIN SOLUTIONS

TECHNICAL FIELD

The present invention generally relates to medical devices and associated methods, systems and computer programs for enhancing software and parameters data integrity. The present invention more particularly relates to ensuring data integrity during updates to medical device software and parameters used by the software.

BACKGROUND

Implantable medical devices are used to monitor physiological parameters and to deliver stimulation signals and/or therapy to selected organs. An external programmer is often used by physicians/technicians to communicate data with an implantable device. The data may include measured parameters, electrocardiograms, markers, instructions, identification information and other such data.

With the advent of far field communications for implantable devices, cloud-based software and/or parameter updates are possible, as are such updates via telemedicine. Whether the data used by the implantable device is set or updated by an external, near-field (e.g. telemetry) programmer or a far field telemedicine or cloud system, it is essential to prevent unauthorized or unintended communications with an implantable device. Such communications, and particularly use of the data from these communications by the implantable device, can result in a minor inconvenience or tragic, life threatening, consequences or any level of risk in between those extremes.

It is public knowledge that Dick Cheney, the former US vice-president, had his heart implant modified for fear of terrorist attack. Mr Cheney's doctor disabled the heart defibrillator's wireless function in 2007 to prevent would-be assassins from interfering with it and causing a fatal heart attack.

In 2008 paper "Pacemakers and Implantable Cardiac Defibrillators: Software Radio Attacks and Zero-Power Defenses", researchers from the University of Washington, the University of Massachusetts Amherst, and Harvard Medical School, claimed that they could carry out software radio-based attacks on ICDs that could "compromise patient safety and patient privacy".

Accordingly, it is desirable to increase data integrity for any updates to implantable medical devices including software and/or treatment parameter updates. In addition, it is desirable to allow patients greater visibility of data integrity enhancements. Furthermore, other desirable features and characteristics of the present invention will become apparent from the subsequent detailed description of the invention and the appended claims, taken in conjunction with the accompanying drawings and the background of the invention.

SUMMARY

In a first aspect, a medical device is provided that is at least partially implantable. The medical device includes an application component configured to apply a therapeutic treatment and/or stimulation signals to a patient, a wireless communications transceiver, and a computer memory storing a parameters library and computer readable instructions. A processor is configured to execute the computer readable instructions so as to:

control application of therapeutic treatment and/or stimulation signals, via the application component, based on parameters stored in the parameters library;

receive, via the wireless communications transceiver, update data representing an update to the parameters library from an external device or system;

transmit at least the update data for verification by a blockchain network and addition of the update data to a verified blockchain public ledger including the update data;

receive, via the wireless transceiver, blockchain public ledger data based on the verified blockchain public ledger;

validate the update to the parameters library based at least on a first condition that the received blockchain public ledger data includes the update data;

when the update to the parameters library is validated, control application of therapeutic treatment and/or stimulation signals, via the application component, based on parameters stored in the parameters library including the update data; and when the update to the parameters library is not validated, control the therapy application component so that the update data is not used.

In a second aspect, a system is provided that includes a blockchain network of computer devices, a first medical device that is at least partly implantable, the first medical device configured to store parameters in a local first medical device parameters library, and an external programmer or a cloud update system configured to set parameters in the local first medical device parameters library via wireless transmission of parameters data to the first medical device. The blockchain network of computer devices is configured to maintain verified blockchain public ledger versions of medical device parameter libraries for each medical device of a distribution of medical devices. The external programmer or the cloud update system is configured to transmit the parameters data to the blockchain network of computer devices. The blockchain network of computer devices is configured to include the parameters data in a verified blockchain public ledger version of a parameters library of the first medical device. The first medical device is configured to retrieve the verified blockchain public ledger version of the parameters library of the first medical device. The first medical device is configured to compare the local first medical device parameters library including the parameters data and the retrieved verified blockchain public ledger version of the parameters library to validate the local first medical device parameters library including the parameters data. The first medical device is configured to, when the local first medical device parameters library has been validated, apply therapeutic treatment and/or stimulation signals to a patient based at least partly on parameters stored in the local first medical device parameters library including the parameters data.

In a third aspect, a method is provided for ensuring data integrity of an implantable medical device. The method includes a blockchain network of computing devices recording parameters or software data transactions with respect to an implantable device in a public ledger, the parameters or software data transactions received over a network from at least one data source. The method includes the implantable medical device receiving updated parameters or software data from a cloud server or an external computing device for storage in a local storage medium. The method includes the implantable medical device installing the updated parameters or software data in the local storage medium when a public ledger version of parameters or software data for the implantable medical device matches a local storage version of parameters or software data for the implantable medical device including the updated parameters or software data. The method includes the implantable medical device not installing the updated parameters or software data in the local storage medium when a public ledger version of parameters or software data for the implantable medical device does not match a local storage version of parameters or software data for the implantable medical device including the updated parameters or software data. The method further includes the implantable medical device configured to use parameters or software data installed in the local storage medium in applying therapeutic treatment and/or stimulation signals to a patient.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Figure 1:
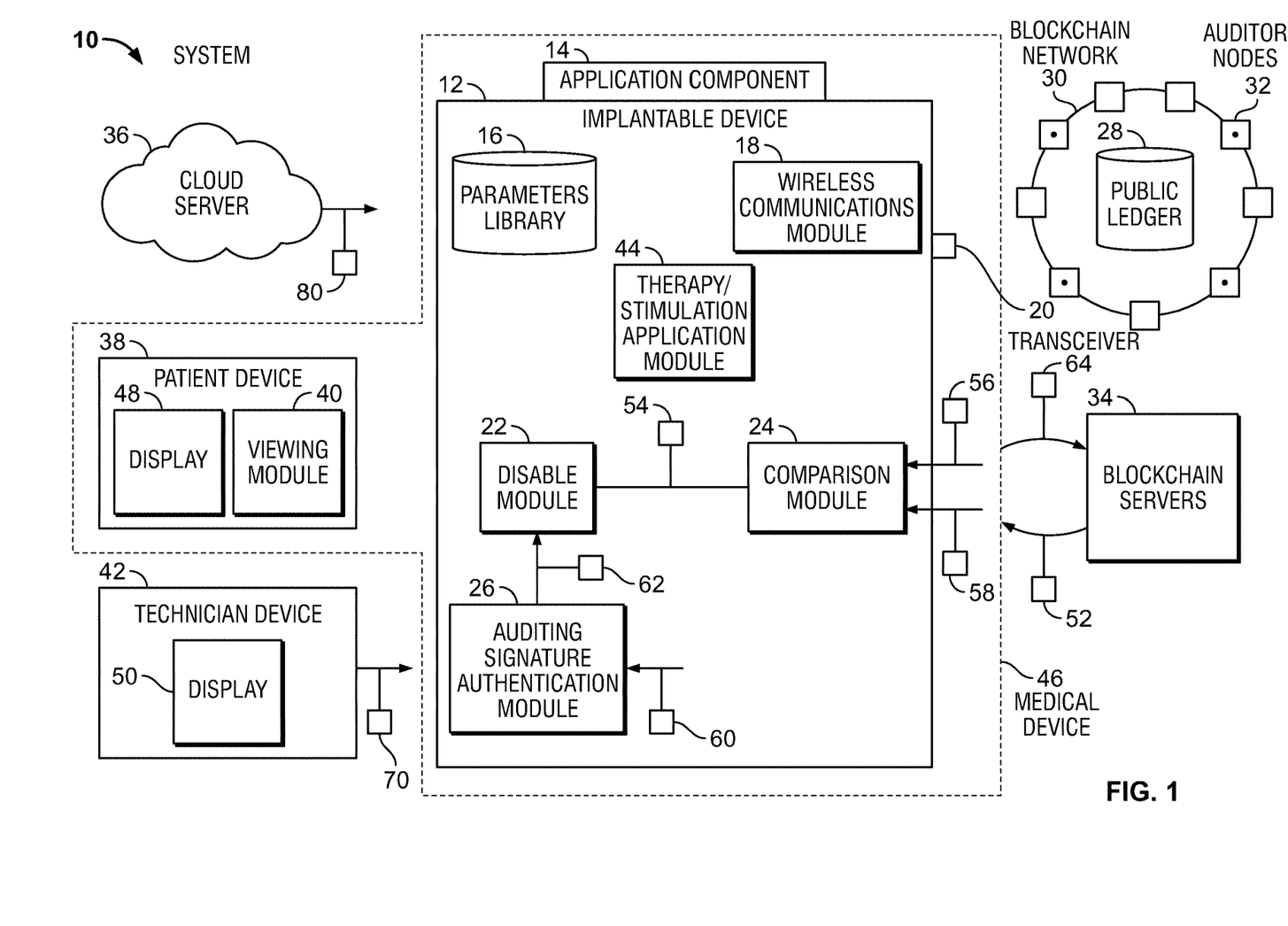
FIG. 1 is a schematic block diagram of a system for ensuring data integrity in an implantable medical device, in accordance with various embodiments.

FIG. 1 is a block diagram representing a system 10 for ensuring integrity of data (including, but not limited to, parameters and software) used by an implantable device 12. In accordance with various embodiments, the system 10 includes an implantable device 12, a blockchain network 30, a blockchain server 34, a cloud server 36, a patient device 38 and a technician device 42. In some embodiments, the implantable device 12 includes memory having stored thereon parameters and software for defining stimulation signals and/or therapeutic treatment to be applied to a patient via an application component 14. The system 10 is configured to ensure integrity of the software programming and/or the parameters by verifying the software programming and/or the parameters based on a public ledger version thereof that is maintained by the blockchain network 30. In embodiments, the public ledger 28 is independently reviewed by an auditor community made up of auditor nodes 32 of the blockchain network 30. According to the systems and methods described herein, updates to the software and/or stimulation/therapeutic application parameters must have been verified by inclusion in the blockchain network and, in some embodiments, verified as audited before being used by the implantable device 12 to generate stimulation signals and/or therapeutic treatment.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Referring back to the system 10 of FIG. 1, the implantable device 12 can be any of a variety of known implantable devices for applying therapeutic treatment and/or stimulation signals to a patient. Exemplary implantable devices include brain implantable devices, such as neural stimulation devices, heart implants, such as defibrillators and pacemakers, artificial kidney implants, etc. In one exemplary embodiment, the implantable device 12 is a deep brain stimulation device, particularly one for applying stimulation signals to white brain matter (e.g. neural axons). The implantable device 12 includes an application component 14 configured to apply therapeutic treatment and/or stimulation signals. In some embodiments, the application component 14 is configured to apply electrical signals to an organ of the patient, such as defibrillation or pacemaker electrotherapeutic signals or deep brain stimulation signals. In other embodiments, the application component 14 applies optical signals to an organ of the patient, such as in optogenetics. In yet other embodiments, the application component 14 is capable of releasing a drug such as insulin into the bloodstream of a patient.

In accordance with various embodiments, the implantable device 12 includes a therapy/stimulation application module 44 configured to generate therapy and/or stimulation application commands that are implemented through the application component 14. In embodiments, the therapy/stimulation application module 44 is configured to issue control commands to a pulse generator or other stimulation signal generator (e.g. optical or electrical) and/or to issue control commands to a drug release circuit. The pulse generator and/or the drug release circuit is responsive to the control commands to apply stimulation signals and/or drug therapy to a patient via the implanted application component. Other circuitry and software components may be included in the medical device 12 in order to apply stimulation signals and/or therapy to the patient via the application component 14. The therapy/stimulation application module 44 is configured to reference a parameters library 16 that is used in defining the stimulation signals and/or the therapeutic treatment. The therapy/stimulation application module 44 is further configured to make use of programming instructions serving to define selection of parameters from the parameters library 16 and the control commands. The programming instructions and/or the parameters library 16 are subject to updates that are only implemented by the implantable device 12 when the public ledger 28 reflects identical data. In embodiments, the therapy/stimulation application module 44 is configured to receive sensor data as inputs and to select parameters from the parameters library and issue the control commands in response thereto.

In an example embodiment where the implantable device 12 is a deep brain stimulation device as described hereinbefore, the application component 14 comprises one or more electrodes located to apply stimulation signals to a patient's brain, such as axons thereof. In embodiments, the implantable device 12 includes a plurality of electrodes and stimulation signals can be applied via various combinations of the plurality of electrodes. Each combination of electrodes can be considered a different channel. Thus, the parameters library 16 includes channel numbers and associated stimulation signal parameters for each channel. The stimulation signal parameters can include signal amplitude (current and/or voltage), signal frequency and/or pulse width. The parameters library 16 further includes, in some embodiments, a stimulation signal meaning field associated with each stimulation signal and channel. The stimulation signal meaning field represents a meaning for the stimulation signal to which the patient has been trained. In this way, an external device (not shown) is able to communicate with the implantable device 12 (via wireless communications module 18 and transceiver 20) and to request that a particular meaning be imparted to the patient from a list of meanings in the parameters library 16. The therapy/stimulation application module 44 of the implantable device 12 is configured to respond thereto and to retrieve the stimulation signal parameters and channel number associated with that meaning from the parameters library 16. The therapy/stimulation application module 44 is configured to issue commands to the pulse generator (not shown) to generate one or more electrical pulses according to the defined stimulation signal parameters and to apply the one or more electrical pulses to the patient at the implant site (the brain in this example) via the corresponding channel of the application component 14. The patient will perceive (consciously or sub-consciously) the stimulation signal and realize (consciously or sub-consciously) the trained meaning.

A deep brain stimulation device has been described in the example above that makes use of stimulation signals and associated meaning. More traditional deep brain stimulation devices apply stimulation signals for therapeutic reasons (rather than imparting a meaning to a patient). These devices are also set with parameters that are kept in a parameters library (e.g. maximum and minimum safety parameters) that would benefit from the data integrity systems and methods disclosed herein. Likewise, parameters kept in a parameters library of a pacemaker would benefit from the enhanced data security methods and systems described herein.

It will be appreciated that the example of deep brain stimulation as the implantable device 12 is but one possibility from a range of implantable medical devices 12 to which the security measures of the present disclosure are applicable. Where there is a possibility for, or a patient fear of, an implantable device 12 to have software or parameters, relating to the application of stimulation signals and/or therapeutic treatment, set or changed in an undesired way (e.g. through hacking or other nefarious control), the teachings of the present disclosure have applicability. For example, it could be dangerous for unauthorized access to heart implant parameters or software that affect stimulation pulses applied to a patient or unauthorized access to software or parameters that affect drug elution from an implantable device. In such cases, more secure control over any initial setting or future changes to parameters and software of an implantable device would be desirable.

In the embodiment of FIG. 1, the implantable device 12 includes a wireless communications module 18 and a transceiver 20 configured to receive communications from various external devices including the patient device 38, the technician device 42, the cloud server 36 and the blockchain server 34. Such communications can be near field (within meters) or far-field (from any remote distance over a network) communications. In embodiments, communications from the technician device 42, the cloud server 36 and/or the blockchain server 34 are sent to the implantable device 12 via the patient device 38 (e.g. indirectly) or directly. As such, the patient device 38 can be considered as part of the same medical device 46 as the implantable device 12. In embodiments, the patient device 12 is a tablet device, a smartphone, a desktop computer, a laptop or a dedicated device for use with the implantable device 12. The patient device 12 includes a display 48. In embodiments, technician device 42 is a tablet device, a smartphone, a desktop computer, a laptop or a dedicated device for use with the implantable device 12 and includes a display 50. The patient device 38 is configured for operation by a patient and includes one or more software applications/modules configured to be operated by a patient to control data communications between the implantable device 12 and the patient device 38. The technician device 42 allows a technician to operate data communications with the implantable device 12 and implantable devices of other patients.

In embodiments, the medical device 46 (e.g. the implantable device 12 or the patient device 38) is configured to communicate with the blockchain network 30 via a blockchain server 34. The wireless communications module 18, or a corresponding module on the patient device 38, is configured to securely send and receive encrypted data to the blockchain server 34. In embodiments, the communications are encrypted and decrypted by PGP algorithms as described further hereinbelow. In embodiments, the blockchain server 34 is a gatekeeper for access to the public ledger 28.

In embodiments, the system 10 includes a cloud server 36 that is able to push data communications to the patient device 38, the technician device 42 or to the implantable device 12. For example, general updates to software and/or parameters of patient's with implantable devices that are to be pushed from the supplier of those implantable devices are sent from the cloud server 36. Such updates are loaded to the implantable device 12 either directly or via the patient device 38 or the implantable device 12 as described in greater detail below.

In order to ensure integrity of data for setting or updates to parameters in parameters library 16 or software run by the implantable device 12, for example software updates to the therapy/stimulation application module 44, the implantable device 12 includes a comparison module 24, an auditing signature authentication module 26, and a disable module 22. In one example, implantable device 12 is configured to receive public ledger data 52 via wireless communications module 18 and transceiver 20. In some embodiments, the public ledger data 52 represents a public ledger version of the parameters library 16 for the implantable device 12 and/or a public ledger representation of the software version being run by the implantable device 12 and/or includes auditing signature data confirming that the auditing community has independently verified the integrity of the public ledger data 52. In embodiments, the comparison module 24 is configured to compare the local version of the parameters library 16 and/or the local software version with the corresponding public ledger data versions 56, 58 represented in the public ledger data 52 and to output comparison result data 54 representing whether a match has been found or not. In embodiments, the auditing signature authentication module 26 is configured to confirm validity of the auditing signature data 60 by checking for presence of an auditing signature and whether the auditing signature is a valid one and to output corresponding result data 62. In accordance with various embodiments, the disable module 22 is configured to be responsive to the comparison result data 54 and/or the auditing signature result data 62 and to disable at least some part of operation of the implantable device 12 when there is a mismatch between the public ledger data 52 and the corresponding local data and/or when received public ledger data 52 is not authenticated by an auditing community through a valid auditing signature. In this way, only software and/or parameters that have been audited by an auditing community (in some examples of the present disclosure) and stored in a blockchain maintained public ledger can be put into operation by the implantable device 12. As such, the patient is protected from any unaudited updates to software or parameters (such as those sent from the cloud server 36 or the technician device 42) that have not passed through the blockchain auditing process.

Figure 2A:
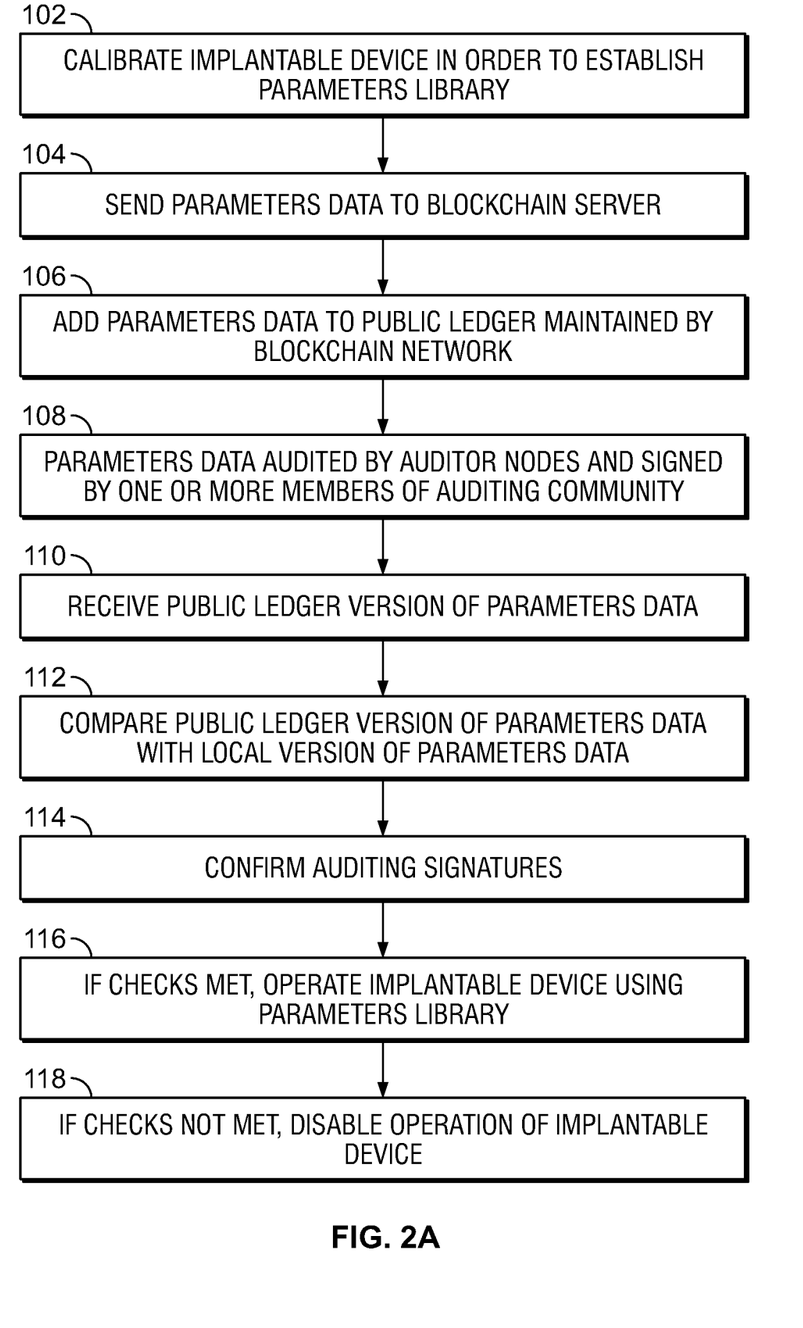
FIGS. 2A to 2C are flow charts of methods of use of the system of FIG. 1, in accordance with various embodiments.
Figure 2B:
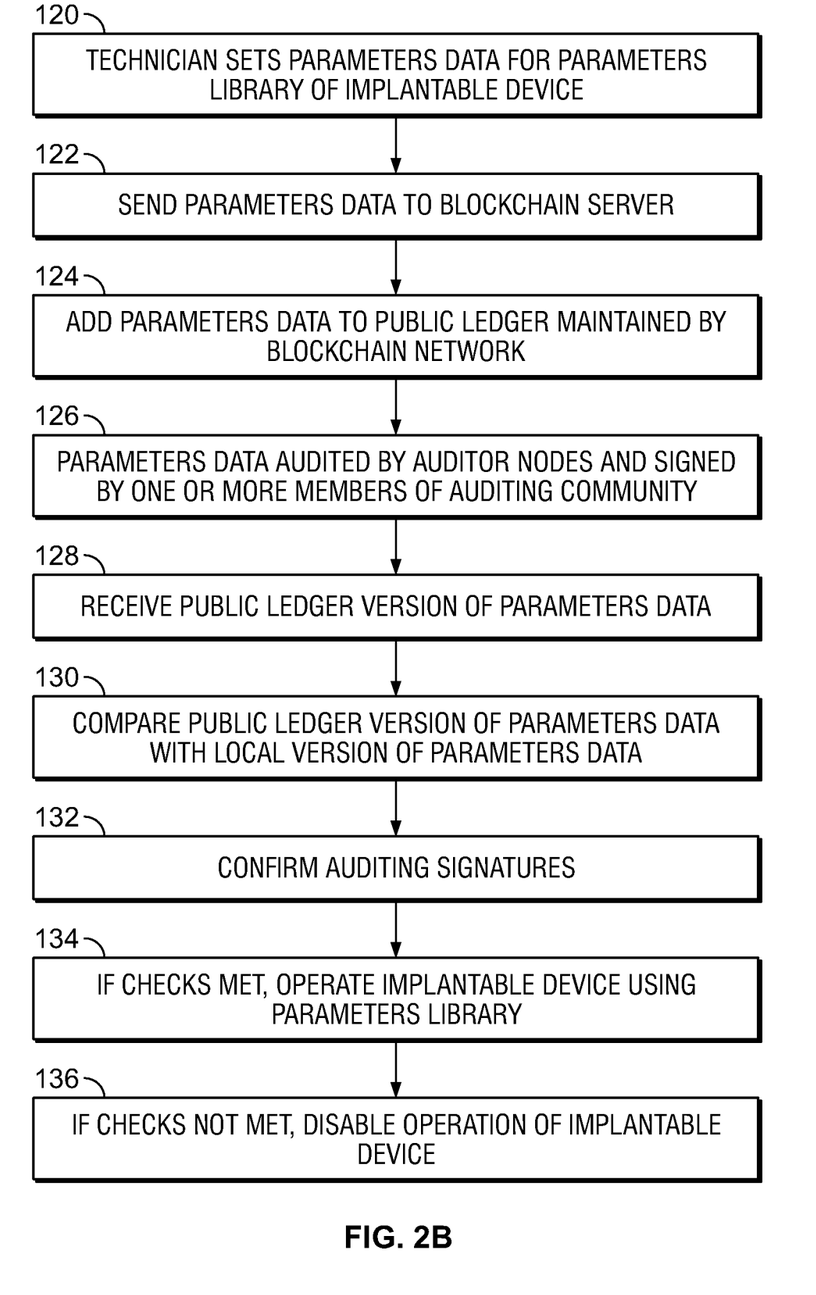
Figure 2C:
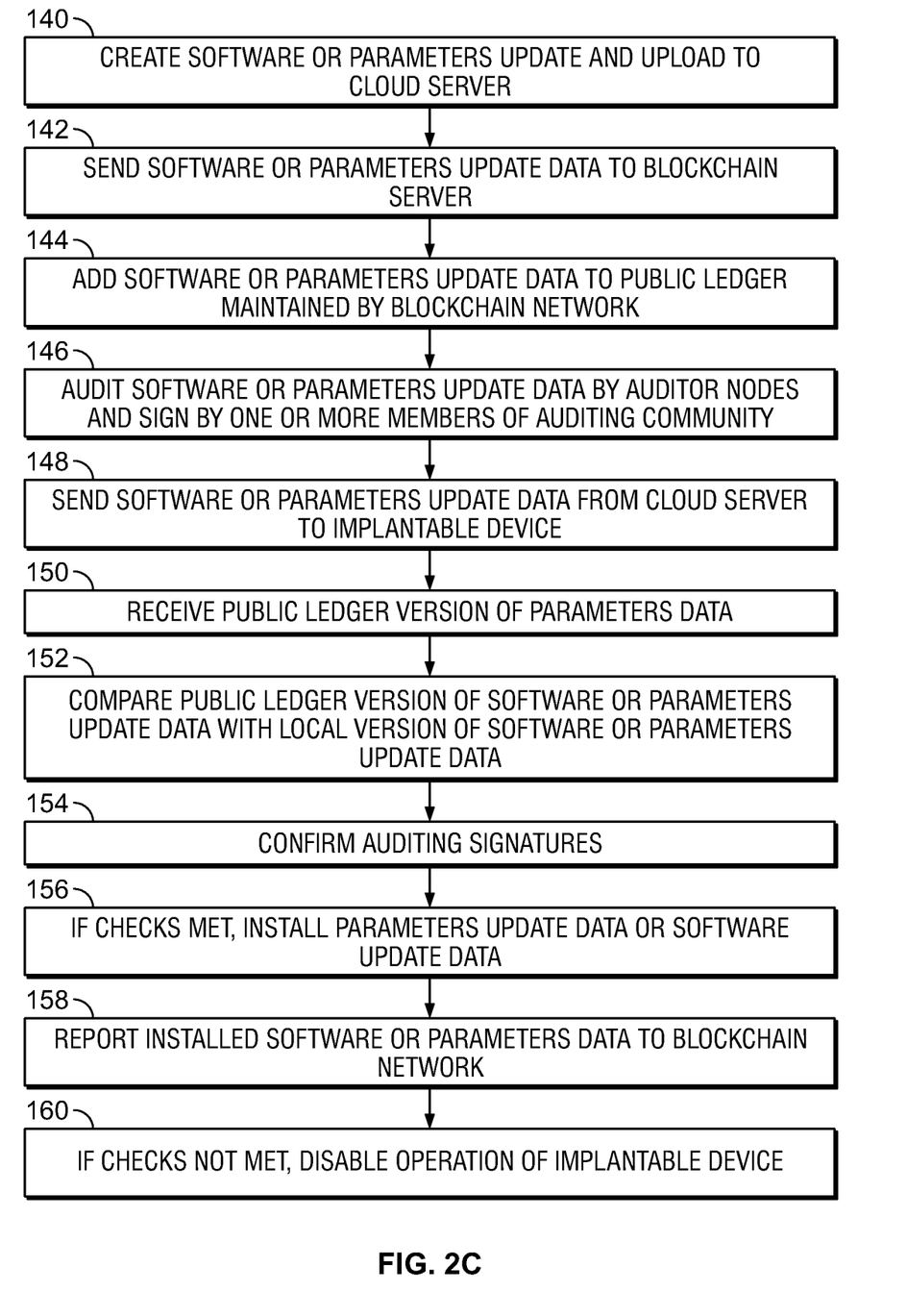

With reference to FIGS. 2A to 2C (and continued reference to FIG. 1), more detailed examples of the security concepts described herein are provided.

FIG. 2A is a flow chart illustrating the security measures described herein in the exemplary use case of a first calibration of an implantable device 12 after implantation. In step 102, the implantable device 12 is calibrated in order to establish the parameters library 16. Step 102 includes, in exemplary embodiments, the technician device 42 (for example) setting various parameters in the parameters library 16 for the first time. For example, a template set of parameters could be initialized in the parameters library 16 and these template parameters are adjusted through the technician device 42 as required for a particular patient. In the example of a deep brain stimulation implantable device 12, each stimulation signal can be defined by a record including various fields that define the stimulation signal parameters (e.g., amplitude, frequency, channel, pulse width, etc.) and a meaning field, which is a trained meaning associated with each different stimulation signal record. For example, the patient can be trained to associate the meaning 'stop' with one stimulation signal and the meaning 'go' with a different stimulation signal. Different stimulation signal parameters will need to be tested and then trained during device calibration step 102 before the parameters library 16 can be established.

In a specific, but merely exemplary, form of step 102, a deep brain stimulation device 12 (for stimulating axons) is implanted and calibrated to the individual patient. As part of that calibration (which stimulation signals elicit desirable responses and which stimulation signals do not elicit desirable responses), a plurality of interpretable stimuli are set. That is, a plurality of records is set in the parameters library 16 that correspond to stimulation signals that can be applied to the patient through the implantable device 12 and which the patient is able to perceive and to differentiate. An exemplary record for one stimulation signal can include stimulation parameters such as stimulation at Contact 1 (channel) with 3/26/35 mA/Hz/PW elicits a response. A second part for each of the plurality of records in the parameters library 16 is established (the meaning part) where the patient is trained to associate each stimulation signal defined in the parameters library 16 with something meaningful, e.g. the warning "STOP". In this way, the parameters library 16 is established as part of the device calibration process in step 102. Different implantable devices will have different calibration processes for establishing a stimulation signal and/or therapeutic treatment parameters library. The present disclosure is not limited by the foregoing example.

In step 104 of FIG. 2A, the parameters library 16, as established in step 102, is sent to the blockchain server 34 for inclusion in the public ledger 28. That is, parameters data 64 from the parameters library 16 is sent to the blockchain server 34. Step 102 is performed by the medical device 46 in some embodiments (e.g. either via the patient device 38 or the implantable device 12) or by the technician device 42 in other embodiments. In embodiments, the device sending the parameters data 64 is configured to encrypt data communications that are sent to the blockchain server 34 and to decrypt data communications that are received from the blockchain server 34. In one example PGP encryption and decryption is used. In this example, the parameters data 64 is encrypted using a private key by the sending device and the private key is encrypted using a public key of the blockchain server 34. The encrypted parameters data 64 and encrypted private key are sent as a message to the blockchain server 34 at which the blockchain server 34 is able to decrypt the encrypted private key using a private key of the blockchain server 34 corresponding to the public key of the blockchain server 34. The unencrypted private key of the sender device can then be used to decrypt the parameters data 64. A corresponding PGP encryption/decryption process can be used for communications from the blockchain server 34 to the implantable device 12.

In accordance with various embodiments, the blockchain server 34 is configured to communicate the decrypted parameters data 64 to the blockchain network 30 for inclusion on the public ledger 28. That is, in step 106, the parameters data 64 is added to the public ledger 28 maintained by the blockchain network 34. The public ledger 28 is in the form of a blockchain, which is a series (or chain) of blocks on which transaction details relating to various implantable devices 12 are recorded after authentication and verification by designated nodes. Transaction details that are recorded include a public ledger version of the parameters library 16 as set in the calibration step 102, any updates to the parameters library 16, software versions (including a history of software update transactions), the source of any transactions (updates) such as technician or patient device ID, etc. The recording and storage of all confirmed transactions on the public ledger 28 starts when the implantable device 12 is calibrated and the parameters library 16 is established in step 102. As understood in the art, when a block is filled to capacity with transaction details, new blocks are mined and are added to the blockchain by network participants called miners. Select network participants maintain a copy of the whole public ledger 28 on their computer devices that are connected to the blockchain network 30. In this way, the public ledger 28 becomes distributed. Since a large number of computer devices (hundreds or thousands or more) of the blockchain network 30 maintain a copy of the public ledger 28, falsification of the public ledger 28 is prevented.

In the example deep brain stimulation use case provided hereinbefore, the parameters data 64 includes an encrypted version of the stimulation signal parameters and the coupled meaning (e.g. a string for each field in the new parameters library 16 comprising PatientXYDATETIME3/26/35 mA/Hz/PW=a="STOP" or a clearer version thereof for understanding by the auditor community described with respect to step 108 below). Such parameters data 64 is submitted by the implantable device 12 by wireless communication using the wireless communications module 18 and the transceiver 20 to the blockchain network 30 (via the blockchain server 34) for recording in the public ledger 28. As such, a public ledger 28 is constructed listing all implantable devices using system 10 and each transaction for each implantable device.

In some embodiments, and according to step 108, the parameters data 64 set by calibration of the implantable device 12 is audited by members of an auditing community at auditing nodes 32 of the blockchain network 30. The auditing process can occur before or after the parameters data 64 is added to the public ledger 28 in step 106. In some embodiments, the blockchain server 34 is configured to electronically notify members of the auditing community when any new transactions are available for auditing. Each auditor member (human) or auditor node (computer device) adds a digital signature to the transaction of adding the parameters data 64 to the public ledger 64 for the implantable device 12 (or other transaction of any implantable device) when the auditor has checked the transaction for correctness.

In accordance with various embodiments, the auditor community is represented by the auditor nodes 32 and includes human auditors checking transactions (parameters data setting or updates or software setting or updates) for reasonableness or undesirable content. The auditor community performs the transactions audit prior to or independent of the authentication and validation of a transaction (update) by designated nodes. In embodiments, each new transaction is audited by one or more auditor nodes (and associated human auditors) and a corresponding auditor or auditors signature is added. The auditors are knowledgeable in the medical field and thus adept at auditing the transactions for implantable devices. In this way, an additional layer of security is added. The public ledger 28 maintained by the blockchain network 30 ensures that each recorded transaction is authentic and the auditor nodes 32 ensure that each recorded transaction is reasonable according to the assessment of an independent auditing community. In some embodiments, each new transaction must be signed by n (where n is a number greater than 1) members of the auditor community before the transaction can be passed to the blockchain network 30 for recording on the public ledger 28. In one embodiment not the entirety of all transactions are audited but only a representative selection of transactions (selected at random, through filters flagging unusual transactions or by active auditor choice), if the coverage of audits per transactions is sufficient this can also be indicated to the user in abbreviated or aggregated form (e.g. in the form of a traffic light system).

In accordance with various embodiments, and according to step 110, the implantable device 12 (or the patient device 38) receives public ledger data 64, which includes a public ledger version of parameters data 56 (e.g. a public ledger version of parameters library). In embodiments, the public ledger data 64 is sent by the blockchain server 34 whenever the blockchain server determines that a new transaction is added to the public ledger 28 associated with the implantable device. In other embodiments, the implantable device 12 (or the patient device 38) is configured to regularly send a request to the blockchain server 34 for the public ledger data 64. For example, either before first activation after the device calibration step 102, or with every recharging cycle or at any chosen interval, the implantable device 12 is set to request the public ledger data 64.

In the embodiment shown in FIG. 2A, the public ledger version of parameters data 56 and the local version of parameters data taken from the parameters library 16 are compared. The comparison is performed through the comparison module 24. In the present use case, the complete public ledger and local versions of the parameters libraries are compared. However, comparison of just part of the parameters libraries is envisaged, such as only new transactions, in other embodiments. The comparison module 24 is configured to output a comparison result 54 (e.g. true or false) indicative of whether the public ledger version of the parameters library 56 and the local version of the parameters library 16 match.

In accordance with some embodiments, step 114 is included in the process, whereby the implantable device 12 (or the patient device 38) is configured to confirm auditing signature data 60 received as part of the public ledger data 64. In embodiments, validity of the auditing signature data is checked (such as determining whether there is a minimum number of auditing signatures by different members of the auditing community such as at least 1, 2, 5, 10, etc.) and are the auditing signatures in the auditing signature data 60 proper. The step 114 is performed by the auditing signature authentication module 26. Auditing signature result data 62 (e.g. true or false) indicative of whether the auditing signature data has been authenticated is passed to the disable module 22.

In accordance with various embodiments, and per step 116 in FIG. 2A, the implantable device 12 is configured to activate operation of the implantable device 12 when the auditing signature result data 62 and the comparison result data 54 indicates that the local and public ledger versions of the parameters libraries 16, 56 are matching and that the public ledger version of the parameters library 56 has been authenticated by the auditing community through proper auditing signature data 60. The implantable device 12 is operated as hereinbefore described whereby therapeutic treatment and/or stimulation signals are generated by the therapy/stimulation application module 44 using the parameters library 16. The generated therapeutic treatment and/or stimulation signals are applied to the patient through the application component 14. Step 116 is performed by disable module 22.

In accordance with various embodiments, and per step 118 in FIG. 2A, the implantable device 12 is configured to disable at least part of application of therapeutic treatment and/or stimulation signals when the auditing signature result data 62 indicates improper auditing signatures and/or the comparison result data 54 indicates a mismatch between the local parameters library 16 and the public ledger version of the parameters library 56.

Thus, according to the method of FIG. 2A, therapeutic treatment and/or stimulation signals are not activated if the loaded parameters library 16 on the implantable device 12 and the corresponding entry in the public ledger 28 are not identical. In the specific deep brain stimulation signal example provided hereinbefore, the methods described herein prevent, that, for example, someone hacks into the implantable device 12 of the patient and changes meanings for a particular stimulation signal (e.g. "STOP" to "GO") without the patient having noticed. The public ledger version of the parameters library 16 cannot be falsified and serves as a safety layer.

Another exemplary use case is described in overview in FIG. 2B, in accordance with various embodiments. In the exemplary embodiment of FIG. 2B, the technician device 42 is configured to push a technician set update to parameters in the parameters library 16 or to push an updated software version of the implantable device 12 (e.g. a version of the software making up the therapy/stimulation application module 44). In one example, a technician visits a patient having the implantable device 12. The technician carries the technician device 42. In other embodiments, the technician and technician device operate remotely (e.g. using a telemedicine system).

In the exemplary embodiment of FIG. 2B, the technician works with the patient to set parameters for the parameters library 16 of the implantable device, according to step 120. The parameters can be additional parameters (e.g. additional fields in the parameters library corresponding to additional stimulation signals and/or additional therapeutic treatments) or revised values of existing parameters. In the specific example provided herein of deep brain stimulation, step 120 includes changing/adapting parameters defining the stimulation signal to, for example, reflect changed physiological conditions (e.g. more mA needed due to impedance changes) or to change parameters defining the trained meaning such as to replace "STOP" with "SLOW DOWN". In this way, parameters data 70 is sent from the technician device 42 to the implantable device 12 (possibly via the patient device 38).

According to step 122, the implantable device 12 or the patient device 38 is configured to send the new/amended parameters data 64, which has been established in step 120, to the blockchain server 34. The new/amended parameters data 64 is based on the parameters library 16 and the parameters data 70 received from the technician device in some embodiments. The new/amended parameters data 64 can be in the form of the entire parameters library 16 with the updated field(s) or just the new/amended parts of the parameters data (e.g. just the affected field(s) of the parameters library 16).

The blockchain server 34 is configured to receive the parameters data 64 and to pass the parameters data 64 to the blockchain network 30 for inclusion in the public ledger 28 in association with the implantable device 12. In exemplary embodiments, the method of FIG. 2B includes a step 124 of adding the parameters data 64 to the public ledger and a step 126 of the parameters data 64 being audited by auditor nodes 32 and signed by one or more members of the auditing community. Steps 124 and 126 have been described above with respect to FIG. 2A with respect to steps 104 and 106. The above description of steps 104 and 106 is applicable to steps 124 and 126.

In FIG. 2B, steps 128 to 132 are similar to steps 110 to 114 described above with respect to FIG. 2A. The implantable device 12 (or the patient device 38) receives public ledger data 52 including parameters data 56 from the blockchain server 34 and the comparison module 24 checks that the public ledger version of the parameters library 56 is identical with the local version of the parameters library 16 including amended/new fields based on the parameters data 70 received from the technician device 42. The auditing signature authentication module 26 checks that the auditing signature data 60 associated with the public ledger data 52 has sufficient and proper signatures from the auditing community. If the checks are met (step 134), the parameters library 16 is updated with the new parameters data 70 from the technician device 42. The therapy/stimulation application module 44 is configured to operate using the parameters library 16 as amended when the checks of steps 130 and 132 have been confirmed.

In the event that at least one of the checks (as embodied in comparison result data 54 and auditing signature result data 62) is negative (step 136), the disable module 22 is configured to disable the therapy/stimulation application module 44 from applying further treatment or stimulation in one embodiment. In another embodiment, only partial disabling is performed. For example, core application of therapy/stimulation is continued based on default programming that does not use the parameters library 16. In other embodiments, the parameters library 16 is not updated with the parameters data 70 (the update is disable by the disable module 22) and the implantable device 12 continues to operate using the parameters library 16 in unamended form.

Thus, in accordance with various embodiments, the implantable device 12 is configured to upload the parameters library 16 including amended or new fields based on parameters data 70 received from technician device 42 to the public ledger 28. The implantable device 12 will not run or, alternatively, save new parameters data 70 or update the parameters library 16 if the implantable device 12 cannot successfully synchronise with the public ledger version of the parameters library 56. Successful synchronization occurs when the public ledger and local version of the parameters library 16, 56 are identical and when the public ledger 28 has been successfully updated and audited.

FIG. 2C illustrates a further exemplary use case in which an update is sent from a cloud server to a plurality of implantable devices. In such a scenario, it is important to verify data integrity and authenticity. The system 10 described herein allows such verification.

In accordance with various embodiments, the method includes step 140 whereby a manufacturer of implantable devices or a service provider for implantable devices or some other enterprise associated with implantable devices creates software or parameters update data 80 and uploads the software or parameters update data 80 to the cloud server 36. In embodiments, step 140 includes creating the software/parameters data 80 for all implantable devices of a particular batch number, a particular list of serial numbers, particular model number or all implantable devices made by the manufacturer or any other grouping of a large collection of implantable devices. The update proceeds through the cloud server 36 in order to address each implantable device in the designated collection of implantable devices (as distinct from individual software or parameter updates performed through technician device 42).

In step 142, the cloud server 36 is configured to send the software or parameters update data 80 to the blockchain server 34. The blockchain server 34 is configured to pass the software or parameters update data 80 to the blockchain network 30 for inclusion in the public ledger 28 as an available cloud update.

In step 144, the blockchain network 30 operates to include the software or update data 80 in the public ledger 28 as an available cloud update. Further, in step 146, the software or update data 80 is audited by the auditor nodes 32 and digitally signed by the auditors at the auditor nodes 32. The auditing step 146 can take place before or after the step 146 of adding the software or update data 80 to the public ledger 28. In this way, the public ledger 28 includes a cloud update transaction comprising update software or parameters data and one or more auditor signatures.

In accordance with various embodiments, the software or parameters update data 80 is sent as a request from the cloud server 36 to the implantable device 12 (optionally via the patient device 38) in step 148. The implantable device 12 accepts the request when certain conditions are met including confirming whether the parameters or software update data is documented in the blockchain public ledger 28. Accordingly, in step 150, the public ledger version 56, 58 of the parameters or software update data is sent from the blockchain server 34 to the implantable device 12 (optionally via the patient device 38) as part of public ledger data 52. In embodiments, the public ledger version of the parameters update data 56 is provided as a complete public ledger version of the parameters library or just the updated parameters data is sent. In embodiments, the public ledger version of the software update data 58 includes software code for a compete module (or modules) or just updated parts of the software code or only a software version identifier is sent.

In accordance with various embodiments, and per step 152, the implantable device 12 (through the comparison module 24) compares the public ledger version of the parameters update data 56 or the public ledger version of the software update data 58 with the corresponding local software or parameters update data 80 received from the cloud server 36 for identicality. Further, sufficiency of auditing signatures data 60 is checked (through the auditing signature authentication module 26) in step 154.

In step 156, assuming the checks of steps 152 and 154 are passed, the parameters library 16 is updated with the parameters update data 80 or one or more software modules (e.g. the therapy/stimulation application module 44) is updated with software update data 80. In accordance with various embodiments, and per step 158, the implantable device 12 (or the patient device 38) is configured to report updated parameters or software data 64 that has been installed in implantable device 12 to the blockchain network 30 for recording in the public ledger 28 as a transaction for the identified implantable device (e.g. including transaction data and a unique implantable device ID).

In step 160, when the auditing signatures data 60 is not sufficient or the comparison module 24 reveals that the cloud update data 80 is not included in the authenticated public ledger 28, the disable module 22 is configured to deny the request for updating software or parameters and the implantable device 12 is configured to continue operation without the update. In embodiments, an update request denial message is sent to the cloud server 36.

In one example of the embodiment of FIG. 2C in a deep brain stimulation context, a required automatic update, such as a safety fix, is designed by a manufacturer and sent to the cloud server 36 for release to all implantable devices of a designated model number. For example, it may have been discovered that all implantable devices must run below 3 mA due to incidents, so all implantable devices have to update entries in the parameters library 16 where 3 mA appears in the "signal". Per step 140, the manufacturer readies the parameters update on its cloud server 36 and submits a copy to the blockchain server 34 for inclusion on the public ledger 28 (according to steps 142 and 144). In step 146, the auditing community audits the update prior to the update being sent out to the implantable device or otherwise being activated. The cloud server 36 then sends the update data 80 to all designated implantable devices in step 148. The implantable device 12 is configured to check that the update is blockchain authenticated (according to steps 150 and 152 and/or 154). After the update in step 156 assuming the checks are met, the updated parameters library 16 is documented together with the complete update history of this patient/implantable device in the blockchain.

According to the various embodiments described herein with respect to FIGS. 1 and 2A to 2C, an implantable device will only operate updated parameters or software when the identical data has been authenticated in the public ledger 28 maintained by a blockchain network 30 and optionally audited by an auditing community. In this way, a patient can be sure of the data integrity of any updated or newly set parameters and software.

In accordance with various embodiments, the patient device 38 includes a viewing module 40. The viewing module 40 could, however, be included on any other appropriate computing device available to the patient. The patient can operate the patient device 38 to enter secure login credentials for submission to the blockchain server 34. The blockchain server 34 is configured to send public ledger data from the public ledger 28 to the patient device 38 for display through the viewing module 40. The sent public ledger data is that corresponding to the patient or the patient's implantable device 12 or implantable devices. The viewing module 40 or the blockchain server 34 is configured to arrange the public ledger data in a patient readable form so that parameters data and software versions included in the public ledger 28 are displayed to the patient on the display under instruction from the viewing module 40.

In embodiments, a patient is able to view his or her own data stored in the public ledger 28 at any time. In some embodiments, the patient is prompted, via a notification on the patient device 38, whenever an update has been sent to the implantable device 12 from the cloud server 36, from the technician device 42 or from any other source. Further, some or all updates may only be installed if they have been confirmed as acceptable by the patient through the patient device 38. That is, the patient is prompted to check the update data in the public ledger and confirms acceptability of that update data before the implantable device 12 will install and run the update. Thus, even if the patient should have been misguided by a nefarious technician, he or she can go on the web (for example) into his user account on the blockchain server 34 and audit what has been written into the public ledger 28 for the implantable device 12 and verify the update. In other embodiments, the patient is informed that a cloud update is available on the patient device 38. The patient could be prompted to make sure that the update is an audited/block chain public ledger documented update through the viewing module 40. In some embodiments, the patient is prompted to agree to the update and can do so with knowledge of what the update entails. In a deep brain stimulation example, the patient could view a "meaning"-switch from "SLOW DOWN" to "JUMP OUT WINDOW" by use of the viewing module 40 for the public ledger 28 and thus could refuse the change by corresponding entry via the patient device 38.

Although parameters have been primarily described with respect to FIGS. 2A to 2C, the present disclosure is similarly applicable to software updates. Indeed, it should be appreciated that any sensitive data or content can be secured by the blockchain authentication methods described herein with respect to FIGS. 1 and 2A to 2C. One additional example could be weights and modes in neural networks. It is conceivable that in the future neuroprosthetic systems and other implantable systems are delivered with pre-trained deep learning neural networks (in pure hardware or software form or combinations thereof such as FPGA chips), which do not vary wildly in their underlying architecture (number of layers, nodes) but perform their different and individualized functions through the individual learning history they pick up over the lifetime of being employed by the user. The data defining the neural network (such as the connection weights in the neural network captured in a sparse adjacency matrix and/or the activation functions of artificial neurons as described by type allocations such as e.g. sigmoid) can be compressed and tracked in the blockchain public ledger 28.

In embodiments described herein, public ledger data 52 received from the blockchain server 34 can be in the form of a hash or checksum or any other uniquely consolidated form of the data included in the public ledger. In such a case, the comparison module 24 compares with a corresponding hash or checksum or the like local version of the data to permit the comparison for identicality. Similarly, the auditing signature data 60 can be a hashed or the like version and the auditing signature authentication module 26 can operate accordingly.

In the embodiments described herein, the comparison module 24, the disable module 22 and the auditing signature authentication module 26 are included as part of the implantable device 12. However, a different distribution of the modules between the patient device 38 and the implantable device 12 could be used. That is, any one or more of the modules 22, 24, 26 could be included in the patient device 38.

Data communications between the various parts of the system 10 of FIG. 1 (e.g. between cloud server 36 and blockchain network 30 and medical device 46) can be performed via cellular network transmissions, over the internet, or by any far field communications means.

While at least one exemplary aspect has been presented in the foregoing detailed description of the invention, it should be appreciated that a vast number of variations exist. It should also be appreciated that the exemplary aspect or exemplary aspects are only examples, and are not intended to limit the scope, applicability, or configuration of the invention in any way. Rather, the foregoing detailed description will provide those skilled in the art with a convenient road map for implementing an exemplary aspect of the invention. It being understood that various changes may be made in the function and arrangement of elements described in an exemplary aspect without departing from the scope of the invention as set forth in the appended claims.

What is claimed is:

1. A medical device that is at least partially implantable, the medical device comprising:
   an application component configured to apply a therapeutic treatment and/or stimulation signals to a patient;
   a wireless communication transceiver;
   a computer memory storing a parameters library and computer readable instructions;
   a processor configured to execute the computer readable instructions so as to:
      control application of therapeutic treatment and/or stimulation signals, via the application component, based on parameters stored in the parameters library;
      receive, via the wireless communications transceiver, update data representing an update to the parameters library from an external device or system;
      transmit at least the update data for verification by a blockchain network and addition of the update data to a verified blockchain public ledger including the update data;
      receive, via the wireless transceiver, blockchain public ledger data based on the verified blockchain public ledger;
      validate the update to the parameters library based at least on a first condition that the received blockchain public ledger data includes the update data;
      when the update to the parameters library is validated, control application of therapeutic treatment and/or stimulation signals, via the application component, based on parameters stored in the parameters library including the update data; and
      when the update to the parameters library is not validated, control the therapy application component so that the update data is not used.

2. The medical device of claim 1, wherein the verified blockchain public ledger includes a verified blockchain version of the parameters library including the update data and validating the update to the parameters library based at least on a first condition comprises validating that the parameters library stored on the computer memory of the medical device matches the verified blockchain version of the parameters library.

3. The medical device of claim 1, wherein the verified blockchain public ledger includes a verified blockchain version of the parameters library and wherein the processor is configured to execute the computer readable instructions so as to:
   periodically validate that the parameters library stored on the computer memory of the medical device matches the verified blockchain version of the parameters library;
   when the parameters library stored on the computer memory of the medical device has been validated, control application of therapeutic treatment and/or stimulation signals, via the application component, based on parameters stored in the parameters library; and
   when the update to the parameters library is not validated, disabling application of therapeutic treatment and/or stimulation signals, via the application component, based on parameters stored in the parameters library.

4. The medical device of claim 1, wherein transmitting at least the update data for verification by a blockchain network comprises encrypting the update data using a transmit private key and encrypting the transmit private key using a blockchain public key received via the wireless transceiver and transmitting the encrypted update data and the encrypted transmit private key.

5. The medical device of claim 1, wherein receiving the blockchain public ledger data comprises receiving encrypted blockchain public ledger data and an encrypted receive private key, the processor configured to execute the computer readable instructions so as to decrypt the encrypted receive private key using a medical device public key and to decrypt the blockchain public ledger data using the decrypted receive private key.

6. The medical device of claim 1, wherein the application component is configured to apply optical and/or electrical and/or electromagnetic stimulation signals to a patient that are controlled at least partly by the parameters library.

7. The medical device of claim 1, wherein the processor is configured to execute the computer readable instructions so as to:
   set patient specific calibration parameters in the parameters library as part of an initial medical device implantation procedure;
   transmit at least the patient specific calibration parameters for verification by a blockchain network and addition of the patient specific calibration parameters to a verified blockchain public ledger including the patient specific calibration parameters.

8. The medical device of claim 1, wherein the application component is configured to apply neuronal stimulation signals.

9. The medical device of claim 8, wherein the parameters library and the update data comprise stimulation signal definition parameters and associated meaning data.

10. A system, comprising:
a blockchain network of computer devices;
a first medical device that is at least partly implantable, the first medical device configured to store parameters in a local first medical device parameters library;
an external programmer or a cloud update system configured to set parameters in the local first medical device parameters library via wireless transmission of parameters data to the first medical device;
the blockchain network of computer devices configured to maintain verified blockchain public ledger versions of medical device parameter libraries for each medical device of a distribution of medical devices;
the external programmer or the cloud update system configured to transmit the parameters data to the blockchain network of computer devices;
the blockchain network of computer devices configured to include the parameters data in a verified blockchain public ledger version of a parameters library of the first medical device;
the first medical device configured to retrieve the verified blockchain public ledger version of the parameters library of the first medical device;
the first medical device configured to compare the local first medical device parameters library including the parameters data and the retrieved verified blockchain public ledger version of the parameters library to validate the local first medical device parameters library including the parameters data;
the first medical device configured to, when the local first medical device parameters library has been validated, apply therapeutic treatment and/or stimulation signals to a patient based at least partly on parameters stored in the local first medical device parameters library including the parameters data.

11. The system of claim 10, wherein the parameters data is calibration parameters set as part of an initial medical device implantation procedure or parameters update data.

12. The system of claim 10, comprising a viewing server configured to remotely host viewing of the verified blockchain public ledger versions of medical device parameter libraries according to secure login data, optionally:
wherein the viewing server is configured to host a patient account that is securely accessible by the patient entering unique login credentials, the viewing server configured to configured to remotely host viewing of the verified blockchain public ledger version of the parameters library associated with the first medical device when the patient account is accessed.

13. The system of claim 10, comprising an auditing server configured to securely host access to the verified blockchain public ledger versions of medical device parameter libraries to an auditor community, wherein the blockchain network of computer devices is configured to require successful auditing reports from at least one member of the auditor community via the auditing server before each update to, or creation of, a medical device parameter library in the verified blockchain public ledger versions of medical device parameter libraries, or
comprising a patient electronic device configured to communicate with the medical device, wherein the medical device is configured to require patient confirmation via the patient electronic device as an additional part of validating the local first medical device parameters.

14. A method for ensuring data integrity of an implantable medical device, the method comprising:
a blockchain network of computing devices recording parameters or software data transactions with respect to an implantable device in a public ledger, the parameters or software data transactions received over a network from at least one data source;
the implantable medical device receiving updated parameters or software data from a cloud server or an external computing device for storage in a local storage medium;
the implantable medical device installing the updated parameters or software data in the local storage medium when a public ledger version of parameters or software data for the implantable medical device matches a local storage version of parameters or software data for the implantable medical device including the updated parameters or software data; and
the implantable medical device not installing the updated parameters or software data in the local storage medium when a public ledger version of parameters or software data for the implantable medical device does not match a local storage version of parameters or software data for the implantable medical device including the updated parameters or software data
the implantable medical device configured to use parameters or software data installed in the local storage medium in applying therapeutic treatment and/or stimulation signals to a patient.

15. The method of claim 14, comprising the implantable medical device installing the updated parameters or software data in the local storage medium when a public ledger version of parameters or software data for the implantable medical device matches a local storage version of parameters or software data for the implantable medical device including the updated parameters or software data and the public ledger version of parameters or software data is digitally signed by at least one member of an independent auditing community; and
the implantable medical device not installing the updated parameters or software data in the local storage medium when a public ledger version of parameters or software data for the implantable medical device does not match a local storage version of parameters or software data for the implantable medical device including the updated parameters or software data or when the public ledger version of parameters or software data is not digitally signed by at least one member of an independent auditing community; or
comprising a patient view the public ledger version of parameters or software data for the implantable medical device using a viewing module executing on a patient computing device; or
wherein the implantable medical device is configured to apply neuronal stimulation signals; or
wherein the at least one data source is a cloud server or a technician device providing parameter or software updates to one or more implantable medical devices.

* * * * *